United States Patent [19]
Grevious

[11] Patent Number: 5,117,825
[45] Date of Patent: Jun. 2, 1992

[54] CLOSED LOOP TRANSMITTER FOR MEDICAL IMPLANT

[76] Inventor: John Grevious, 2239 Wilson St., NE., Minneapolis, Minn. 55418

[21] Appl. No.: 611,900

[22] Filed: Nov. 9, 1990

[51] Int. Cl.⁵ ............................................. A61N 1/37
[52] U.S. Cl. ............................ 128/419 PG; 128/903
[58] Field of Search ................ 128/419 PG, 696, 903; 600/13-15

[56] References Cited

U.S. PATENT DOCUMENTS

| | | | |
|---|---|---|---|
| 4,562,840 | 1/1986 | Batina et al. | 128/903 |
| 4,654,574 | 3/1987 | Thaler | 500/14 |
| 4,679,560 | 7/1987 | Galbraith | 128/903 |

OTHER PUBLICATIONS

Donaldson, N. "Medical & Biological Engineering & Computing", vol. 23, No. 3, May 1985, p. 291.
Kadefors, R. "I.E.E.E. Transactions on Biomedical Engineering" vol. 23, No. 2, Mar., 1976, pp. 124-129.

Primary Examiner—William E. Kamm
Attorney, Agent, or Firm—Harold R. Patton; John A. Rissman; John L. Rooney

[57] ABSTRACT

A technique for improving the radio frequency coupling between an external programming device and a medical device implanted within a patient. The radio frequency coupling is typically used to non-invasively change the operating parameters of the implanted device, such as a cardiac pacer. A common frequency for transmission is 175 khz. At this frequency, in view of the low power and the short distances involved, positioning of the external antenna with respect to the implanted antenna becomes critical. This criticality is heightened because of the great change in transmitter antenna loading and tuning with small changes in relative position.

To assist the attending medical personnel, the transmitter antenna is ordinarily mounted within a paddle-like structure. A feedback coil is placed within the same physical package. The signal induced within the feedback coil is amplified, filtered, and integrated to produce a signal which controls the output amplifier of the transmitter. In this manner, a constant output field strength is provided, even though slight changes in physical position modifies output loading.

10 Claims, 6 Drawing Sheets

CLOSED LOOP TRANSMITTER FOR MEDICAL IMPLANT

CROSS REFERENCE TO CO-PENDING APPLICATIONS

This patent application relates to U.S. patent application Ser. No. 07/612,046, filed Nov. 9, 1990, entitled "Method and Apparatus for Processing Quasi-Transient Telemetry Signals in Noisy Environments" to the same assignee as this patent application.

BACKGROUND OF THE INVENTION

1. Field of the Invention

The present invention generally relates to implantable medical devices, and more particularly, relates to techniques for controlling implantable devices.

2. Description of the Prior Art

As implantable medical devices in general and cardiac pacers in particular became more complex in operation, the desirability for non-invasive transfer of data between the implant and an external device could be seen. In cardiac pacing, transfer of signals from an external device to the implant to modify operating parameters is called programming. Data is also transferred from the cardiac pacer to the external device to provide various monitoring information. These transfers are often termed telemetry.

U.S. Pat. Nos. 4,142,533 and 4,332,256 both issued to Brownlee et al., describe one approach to data communication between an implanted cardiac pacer and an external device. Though the primary feature discussed is telemetry of monitoring data from the implant, the importance of a non-invasive approach is emphasized.

A specifically two-way transmission system is shown in U.S. Pat. No. 4,231,027 issued to Mann et al. A similar system is shown in U.S. Pat. No. 4,324,251 issued to Mann. From these references, it can be seen that close proximity of receiver and transmitter is anticipated. In U.S. Pat. No. 4,556,061 issued to Barreras et al., the use of either magnetic coupling or radio frequency signals is discussed.

From all of these references, it is clear that the current state of the art is to transfer signals between an external programming device and an implanted medical device using a radio frequency carrier employing very close spacing of the transmitting and receiving antennae. Such close spacing provides low power operation for a given minimum signal to noise ratio in accordance with the well known inverse square law.

Unfortunately, this close spacing causes the metallic case of the cardiac pacer, along with the enclosed receiving antenna, to have a major impact upon transmitter antenna tuning and loading. In practice, this means that small changes in positioning of the external antenna (the position of the implanted antenna is assumed to be fixed) can cause large percentage changes in the interantenna spacing. The result is that transmitter antenna loading varies greatly from patient to patient and even within a single transmission for a particular patient if the transmitter antenna is moved even slightly. Antenna tuning is similarly effected by the relative change of position of the implanted pulse generator within the transmitter field.

SUMMARY OF THE INVENTION

The present invention overcomes the disadvantages found in the prior art by providing a transmitting system which generates a radio frequency signal of constant field strength, notwithstanding changes in loading caused by changes in position of the transmitting antenna relative to the receiving antenna. Such control of the field strength of the transmission ensures constant field strength in view of normal variance in component values during the manufacturing process.

To accomplish the objects of the present invention, a separate feedback sense coil is placed in the same package as the transmitting antenna. In most cases this is a paddle-like transmission head which is electrically coupled to the external programmer electronic circuits. The feedback sense coil receives a signal which is proportional to the transmission field strength. The relative positioning of the transmitting antenna and the feedback sense coil is fixed by the design of the transmission head.

The signal received by the feedback sense coil is detected, filtered, and amplified to produce a control signal indicative of the field strength of the transmitted signal. This control signal is used to adjust the gain of the radio frequency output amplifier to maintain a constant field strength of the transmission.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the FIGURES thereof and wherein.

DETAILED DESCRIPTION OF THE PREFERRED EMBODIMENTS

Figure 1:
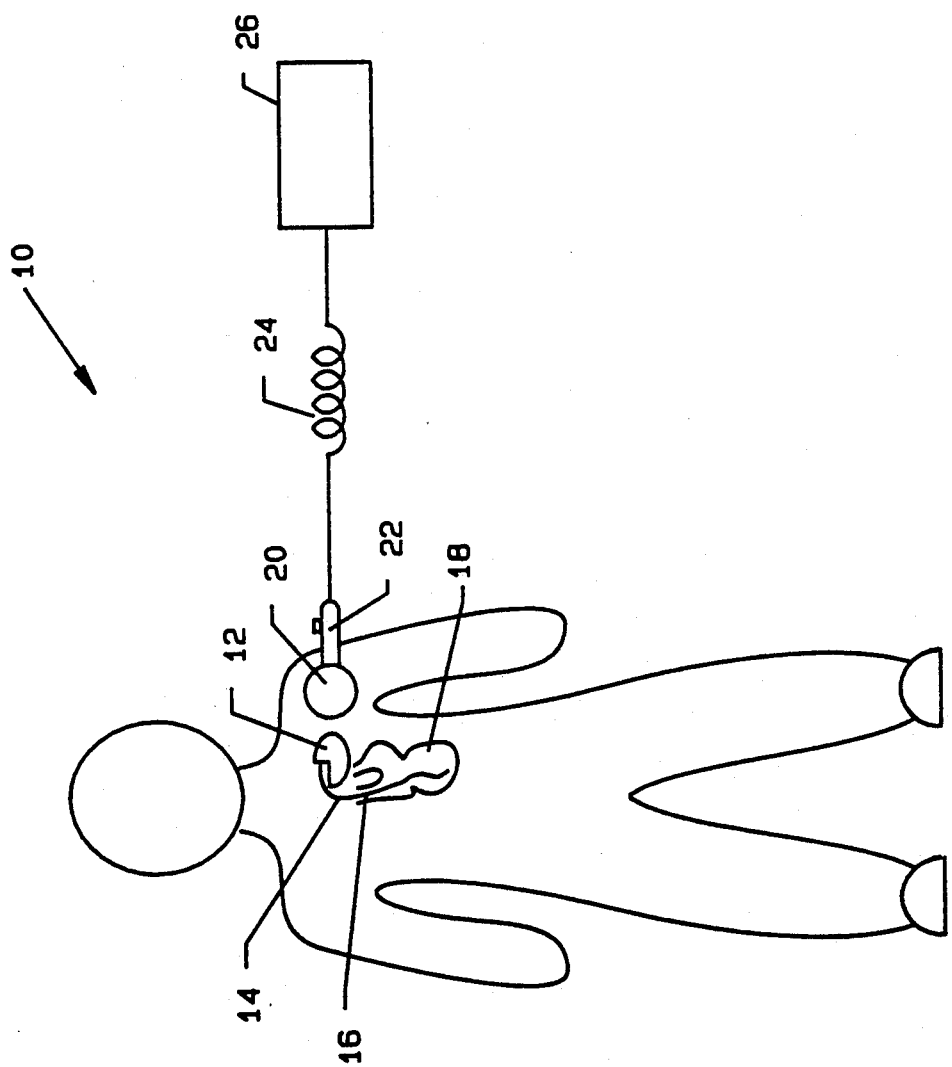
FIG. 1 is a conceptual diagram of a cardiac pacing system employing the present invention.

FIG. 1 is a conceptual view of a cardiac pacing system used to treat patient 10. Implantable pulse generator 12 is implanted beneath the skin of patient 10 in the upper chest region. It is electrically coupled via insulated pacing lead 14 through the venous system 16 to heart 18.

The operating parameters of implantable pulse generator 12 are non-invasively programmed by the attending medical personnel using the electronic circuitry of external programmer 26. A control signal is sent from external programmer 26 via cord 24 to transmission head 20. This control signal causes the electronic circuitry within transmission head 20 to generate the radio frequency signal.

To program implantable pulse generator 12, the attending medical personnel enter the parameter data into external programmer 26. Transmission head 20 is placed on the skin of patient 10 in close proximity to implantable pulse generator 12. The button shown positioned on operator handle 22 is pressed to enable transmission of the programming data via the radio frequency carrier.

Figure 2:
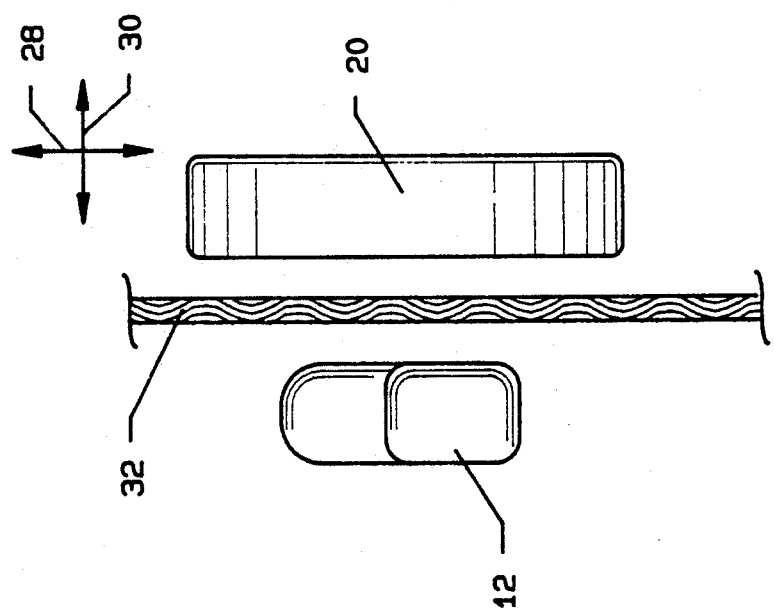
FIG. 2 is an end view of the relative positioning of the implanted device and transmission head.

FIG. 2 is a cutaway end view of the relative positions of implantable pulse generator 12 and transmission head 20. Ordinarily, the transmitting antenna within transmission head 20 and the receiving antenna within implantable pulse generator 12 will not be separated by much more than the thickness of skin layer 32 (FIG. 2 shows a slight separation for clarity).

Under normal conditions, implantable pulse generator 12 will be stationary with respect to skin layer 32 because the implant has been properly sutured into place and subsequent biological growth maintains this position chronically. Transmission head 20 similarly can not move significantly in the direction of arrow 30 if it is to rest on skin layer 32. However, transmission head 20 is free to move in the direction of arrow 28 and in the direction of a line (not shown) which is mutually perpendicular to arrows 28 and 30. This may be caused by the medical attendant as a result of misplacement of transmission head 20 or may even occur during a transmission by physical movement of transmission head 20.

It is apparent that the metallic enclosure of implantable pulse generator 12 is sufficiently close to transmission head 20 during transmission to significantly effect its tuning and loading characteristics. Movement along arrow 28 or along the line mutually perpendicular to arrows 28 and 30 will, therefore, greatly impact transmission performance.

Figure 3:
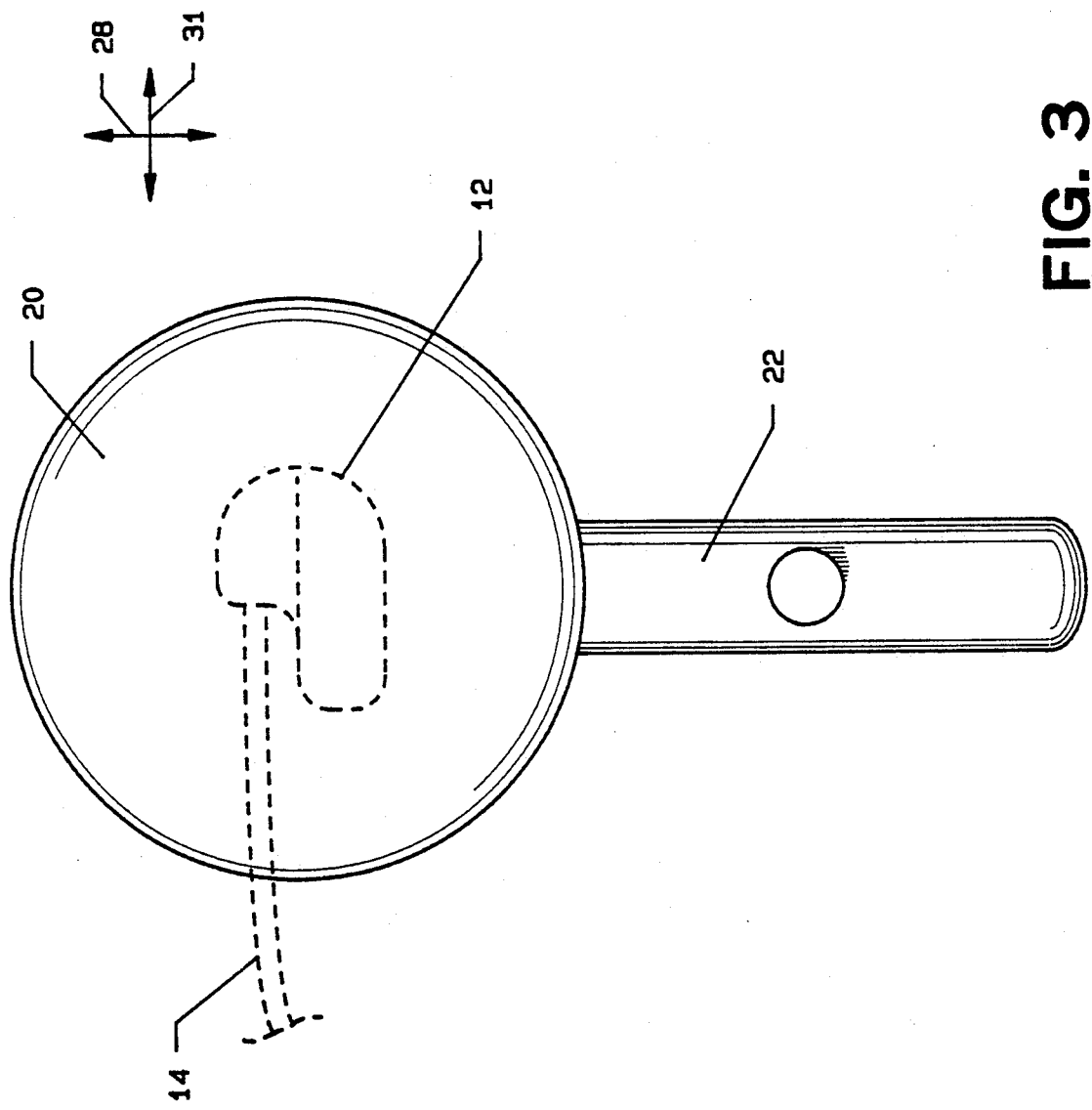
FIG. 3 is a top view of the relative positioning of the implanted device and transmission head.

FIG. 3 is a top view of transmission head 20 as positioned over implantable pulse generator 12 (shown in phantom). It can be seen in this view that the medical attendant is free to move transmission head 20 in the plane of arrow 28 and line 31 (i.e. the line mutually perpendicular to arrows 28 and 30, see also FIG. 2). Such movement will clearly impact the centering of implantable pulse generator 12 within the transmitting antenna (not shown) of transmission head 20. The loading of this transmitting antenna is thereby changed because of the close proximity of implantable pulse generator 12.

Figure 4:
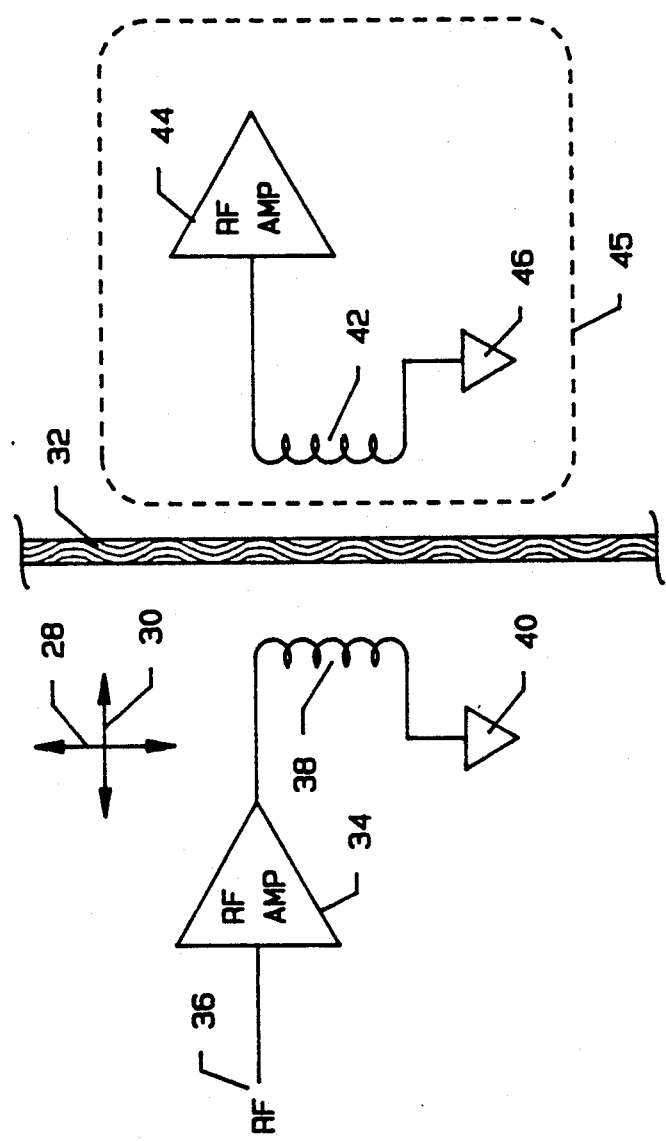
FIG. 4 is a schematic diagram of the major transmission components.

FIG. 4 is an electrical schematic of the key component which serve to transfer data between external programming device and implantable pulse generator through skin layer 32. The modulated radio frequency signal 36 is supplied to radio frequency amplifier 34. The amplified signal is conducted through transmitting antenna 38 to signal ground 40.

The electromagnetic field generated by transmitting antenna 38 induces a radio frequency signal in receiving antenna 42 between radio frequency amplifier 44 and signal ground 46. The output of radio frequency amplifier 44 is demodulated and processed in the manner known in the art.

In accordance with the previous discussion, the loading and tuning, and therefore, impedance of transmitting antenna 38 is effected by the close proximity of receiving device shield 45 and receiving antenna 42. This in part determines the current which flows in transmitting antenna 38, and thereby the strength of the resulting electromagnetic field A change in the strength of this electromagnetic field changes the strength of the signal induced within receiving antenna 42, thus changing the signal level of the received signal.

Figure 5:
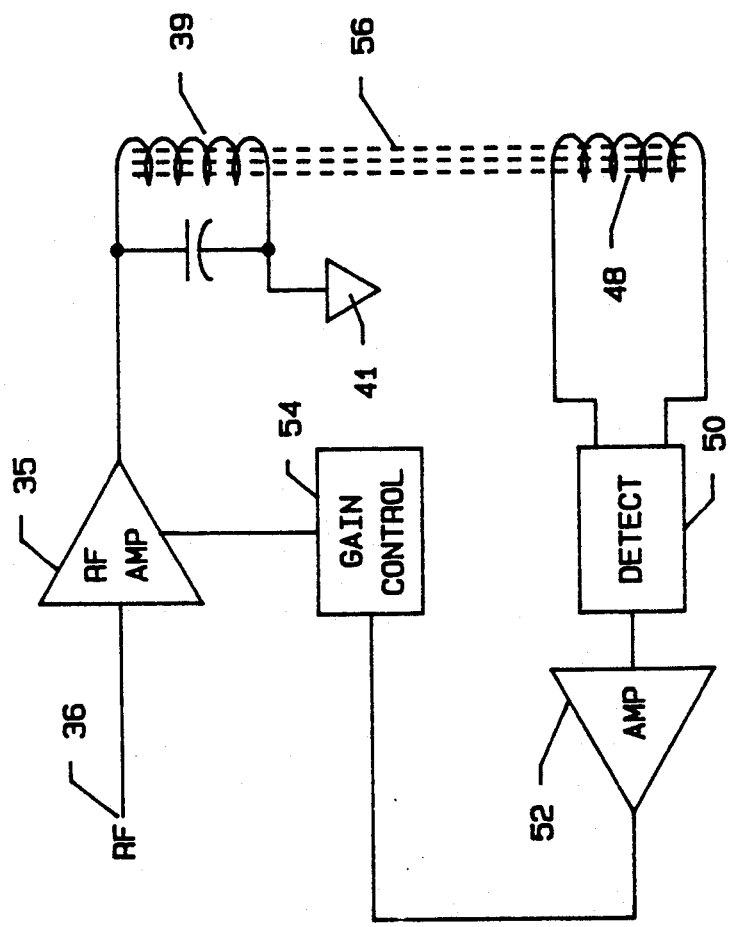
FIG. 5 is a schematic diagram of the feedback loop of the present invention; and, FIG. 6 is an exploded view of the transmission head of the present invention.

FIG. 5 is a schematic diagram of the key components added to the transmitter to practice the present invention in the preferred embodiment. Modulated radio frequency signal 36 is amplified by variable gain radio frequency amplifier 35 operating in class "C" in conjunction with the tuned antenna. The amplified output current oscillates between transmitting antenna 39 and tuning capacitor 43. Core 56 is shared with sensing feedback antenna 48 to ensure close and fixed coupling of transmitting antenna 39 and sensing feedback antenna 48.

The signal induced in sensing feedback antenna 48 as a result of this coupling is proportional to the current flowing in transmitting antenna 39. This induced signal is detected by detector 50. The output of detector 50 is amplified by amplifier 52 and is used to control the variable gain of radio frequency amplifier 35 via gain control 54. The object of this control is to maintain a constant radio frequency current within transmitting antenna 39 during transmission. This constant current ensures a constant electromagnetic field notwithstanding the loading impact caused by the close proximity of the receiving antenna.

Figure 6:
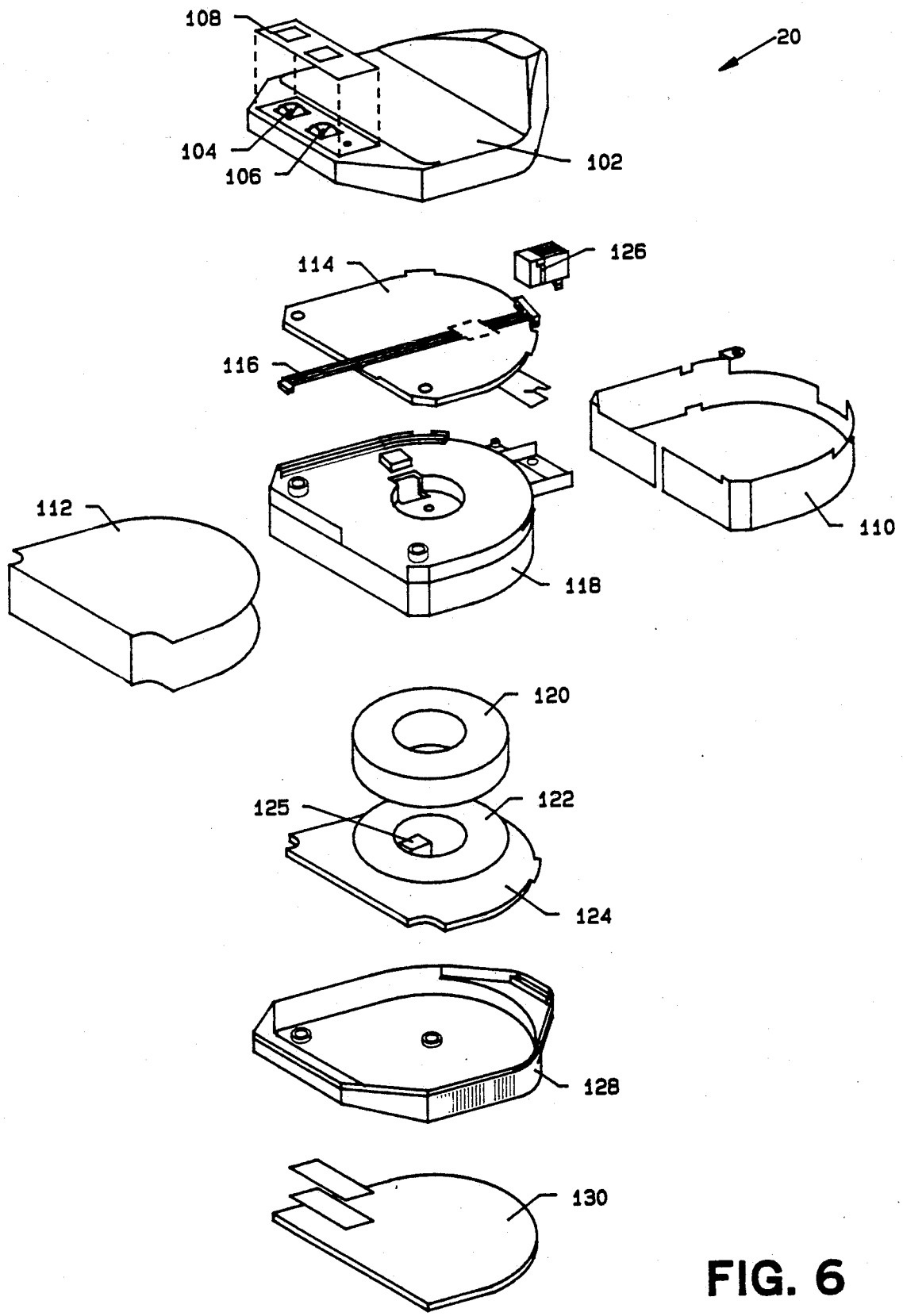

FIG. 6 is an exploded view of the transmission head 20. The outer case comprises the upper case member 102 which attaches to lower case member 128. Upper case member 102 contains operator push buttons 104 and 106, which are coupled to printed circuit board 114 by connector assembly 116. Printed circuit board 114 contains the electronic circuitry to generate and control the radio frequency signal. Planar shield 112 provides shielding at the upper and lower surfaces of printed circuit board 114. Edge shield 110 provides similar shielding at the edges of the package.

Printed circuit board 124 contains the transmitting antenna 39 and feedback antenna 48, both of which are deposited and photoetched on the insulated printed circuit substrate. Printed circuit board 114 and printed circuit board 124 are electrically coupled via connector assembly 125 through the center of retainer 118. Connector assembly 126 electrically couples transmission head 20 to cord 24.

Magnet 120 is used to activate the reed switch located in the implanted pulse generator as is known in the art. Insulator 122 is used to insulate printed circuit board 124 from magnet 120. Retainer 118 provides the internal form into which the interior components are placed. Label 130 is adhesively attached to the underside of transmission head 2 to provide some key operational details.

Having thus described the preferred embodiments of the present invention, those of skill in the art will be readily able to apply the teachings found herein to yet other embodiments within the scope of the claims hereto attached.

I claim:

1. In a cardiac pacing system having an implantable pulse generator with a radio frequency receiving antenna and having an external programmer with a transmitting antenna, said implantable pulse generator having circuitry which is programmed by placing said transmitting antenna in close proximity to said receiving antenna and transferring data between said transmitting antenna and said receiving antenna via a radio frequency carrier generated by said external programmer, the improvement comprising:
   a. means coupled to said external programmer for maintaining a constant electromagnetic field generated by said radio frequency carrier.

2. The improvement of claim 1 wherein said maintaining means further comprises a sensing feedback antenna for measuring said constant electromagnetic field.

3. The improvement of claim 2 said sensing feedback antenna for closely coupling to said transmitting antenna.

4. The improvement of claim 3 wherein said maintaining means further comprises electronic circuitry coupled to said sensing feedback antenna for controlling a constant current of said radio frequency carrier through said transmitting antenna based upon radio frequency energy induced in said sensing feedback antenna.

5. The improvement of claim 4 further comprising a substrate wherein said sensing feedback antenna and said transmitting antenna are fabricated on said substrate.

6. A method of maintaining a constant electromagnetic field generated by a transmitting antenna comprising:
 a. sensing said generated electromagnetic field with a sensing feedback antenna in close proximity to said transmitting antenna;
 b. developing a control signal from said sensing; and,
 c. controlling said electromagnetic field in response to said control signal.

7. An apparatus comprising:
 a. means for transmitting a radio frequency signal;
 b. means for receiving a radio frequency signal positioned in such close proximity to said transmitting means that said receiving means has an impact on loading of said transmitting means; and,
 c. means responsively coupled to said transmitting means for maintaining a constant strength electromagnetic field of said radio frequency signal.

8. An apparatus according to claim 7 wherein said maintaining means further comprises a sensing feedback antenna positioned in close proximity to said transmitting means for monitoring said constant strength electromagnetic field.

9. An apparatus according to claim 8 wherein said maintaining means further comprises feedback circuitry coupled to said sensing feedback antenna and said transmitting means whereby said constant strength electromagnetic field is generated.

10. An apparatus according to claim 9 wherein said transmitting means further comprises a substrate having a transmitting antenna on which said sensing feedback antenna is fabricated.

* * * * *